US00PP13679P29

(12) United States Plant Patent
Hill, Jr.

(10) Patent No.: US PP13,679 P2
(45) Date of Patent: Mar. 25, 2003

(54) GUZMANIA PLANT NAMED 'VIOLA'

(75) Inventor: Herbert H. Hill, Jr., Lithia, FL (US)

(73) Assignee: Twyford International Inc., Santa Paula, CA (US)

( * ) Notice: Subject to any disclaimer, the term of this patent is extended or adjusted under 35 U.S.C. 154(b) by 0 days.

(21) Appl. No.: 10/142,840

(22) Filed: May 10, 2002

(51) Int. Cl.[7] ..... A01H 5/00
(52) U.S. Cl. ..... Plt./371

(58) Field of Search ..... Plt./371

*Primary Examiner*—Kent Bell
(74) *Attorney, Agent, or Firm*—C. A. Whealy

(57) ABSTRACT

A new and distinct cultivar of Guzmania plant named 'Viola', characterized by its upright and outwardly arching plant habit; medium green-colored foliage; inflorescences held upright and above foliage on strong scapes; branched inflorescences with showy red purple flower bracts; and long-lasting inflorescences that maintain good coloration for about two to three months.

1 Drawing Sheet

BOTANICAL CLASSIFICATION/CULTIVAR DESIGNATION

*Guzmania alborosea*×(*Guzmania lingulata*×*Guzmania lingulata* var. *minor*) cultivar 'Viola'.

BACKGROUND OF THE INVENTION

The present Invention relates to a new and distinct cultivar of Guzmania plant, botanically known as *Guzmania alborosea*×(*Guzmania lingulata*×*Guzmania lingulata* var. *minor*) and referred to by the cultivar name 'Viola'.

Guzmania is native to tropical America. Leaves of the Guzmania are usually formed as basal rosettes which are stiff and arranged in several vertical ranks. Guzmania have terminal flower spikes of panicles which are often bracted with petals united in a tube about as long as the calyx.

The new Guzmania is a product of a planned breeding program conducted by the Inventor in Lithia, Fla. The objective of the breeding program is to create new Guzmania cultivars with a plant habit appropriate for container production, desirable flowering habit and inflorescence coloration, and good postproduction longevity.

The new Guzmania originated from a cross made by the Inventor in Lithia, Fla. in March, 1993, of an unidentified selection of *Guzmania alborosea*, not patented, as the female, or seed, parent with the *Guzmania lingulata*× *Guzmania lingulata* var. *minor*) cultivar Ultra, disclosed in U.S. Plant Pat. No. 8,221, as the male, or pollen, parent. The cultivar Viola was discovered and selected by the Inventor as a flowering plant within the progeny of the stated cross in a controlled environment in Lithia, Fla., in June, 1996.

Asexual reproduction of the new Guzmania by off-shoots in a controlled environment in Lithia, Fla. since October, 1996, has shown that the unique features of this new Guzmania are stable and are reproduced true to type in successive generations. Asexual reproduction of the new Guzmania by tissue culture done in a laboratory in Sebring, Fla. since June, 1998, has also confirmed that the unique features of this new Guzmania are stable and are reproduced true to type in successive generations.

SUMMARY OF THE INVENTION

The new Guzmania has not been observed under all possible environmental conditions. The phenotype may vary somewhat with variations in environment such as temperature and light intensity without, however, any variance in genotype.

The following characteristics have been repeatedly observed and are determined to be basic characteristics of 'Viola' and distinguish 'Viola' as a new and distinct cultivar:

1. Upright and outwardly arching plant habit.

2. Medium green-colored foliage.

3. Inflorescences held upright and above foliage on strong scapes.

4. Branched inflorescences with showy red purple flower bracts.

5. Long-lasting inflorescences that maintain good coloration for about two to three months.

Plants of the new Guzmania can be compared to plants of the female parent, the unidentified selection of *Guzmania albarosea*. In side-by-side comparisons conducted in Lithia, Fla., plants of the new Guzmania differed from plants of the female parent in the following characteristics:

1. Plants of the new Guzmania had lighter green-colored leaves than plants of the female parent.

2. Plants of the new Guzmania had shorter inflorescence spikes than plants of the female parent.

3. Plants of the new Guzmania had red purple-colored flower bracts whereas plants of the female parent had pink-colored flower bracts.

Plants of the new Guzmania can be compared to plants of the male parent, the cultivar Ultra. In side-by-side comparisons conducted in Lithia, Fla., plants of the new Guzmania differed from plants of the cultivar Ultra in the following characteristics:

1. Plants of the new Guzmania were larger than plants of the cultivar Ultra.

2. Plants of the new Guzmania had longer inflorescence spikes than plants of the cultivar Ultra.

3. Plants of the new Guzmania had red purple-colored flower bracts whereas plants of the cultivar Ultra had dark purple-colored flower bracts.

Of the commercial Guzmania cultivars known to the Inventor, none compare well to the new Guzmania due to its unique flower bract coloration.

BRIEF DESCRIPTION OF THE PHOTOGRAPH

The accompanying colored photograph illustrates the overall appearance of the new Guzmania, showing the colors as true as it is reasonably possible to obtain in colored reproductions of this type. Colors in the photograph may differ slightly from the color values cited in the detailed botanical description which accurately describe the colors of the new Guzmania. The photograph comprises a side perspective view of a typical flowering plant of 'Viola' grown in a container.

DETAILED BOTANICAL DESCRIPTION

The aforementioned photograph and following observations, measurements, values, and comparisons describe plants grown in Lithia, Fla., under a polyethylene-covered greenhouse and conditions which closely approximate those used in commercial practice. During the production of the plants, day temperatures ranged from 70 to 90° F., night temperatures ranged from 65 to 75° C., and light levels were about 1,500 to 2,000 foot-candles. Single plants used for the photograph and for the description were about 12 months old and grown in 15-cm containers. Color references are made to The Royal Horticultural Society Colour Chart, 1995 Edition, except where general terms of ordinary dictionary significance are used.

Botanical classification: *Guzmania alborosea*×(*Guzmania lingulata*×*Guzmania lingulata* var. *minor*) cultivar Viola.

Parentage:

*Female, or seed, parent.*—Unidentified selection of *Guzmania alborosea*, not patented.

*Male, or pollen, parent.*—*Guzmania lingulata*× *Guzmania lingulata* var. *minor*) cultivar Ultra, disclosed in U.S. Plant Pat. No. 8,221.

Propagation:

*Type.*—By tissue culture.

*Time to initiate roots on tissue-cultured plants.*—Summer: About 14 days at day temperatures of 70 to 90° F. and night temperatures of 65 to 75° F. Winter: About 14 to 18 days at day temperatures of 70 to 90° F. and night temperatures of 65 to 75° F.

*Time to produce a rooted tissue-cultured plant.*—Summer: About 140 days at day temperatures of 70 to 90° F. and night temperatures of 65 to 75° F. Winter: About 150 days at day temperatures of 70 to 90° F. and night temperatures of 65 to 75° F.

*Root description.*—Fine, wiry, fibrous; moderate branching; initially greenish white becoming brown in color.

Plant description:

*General appearance.*—Upright and outwardly arching plant habit. Closely layered strap-like leaves arranged in a basal rosette. Appropriate for 15-cm containers. Vigorous growth habit.

*Plant height, soil surface to top of inflorescence.*—About 43 to 47 cm.

*Plant diameter or spread.*—About 70 to 78 cm.

*Foliage description.*—Arrangement: Basal rosette, spiral phyllotaxis; sessile. Quantity of leaves per plant: Plants typically produce about 30 leaves before inflorescence development. Shape: Ligulate. Apex: Acute. Margin: Entire. Length: About 45 to 50 cm. Width: About 3.8 to 4.3 cm; width at base, about 6.5 cm. Aspect: Blade, channeled; leaves curved downward. Texture, upper and lower surfaces: Leathery, stiff; glabrous. Venation: Parallel. Leaf sheath: Not observed. Color: Young and fully expanded leaves, upper surface: More green than, but closest to 137A; towards the base, striations of 187A to 187B. Young and fully expanded leaves, lower surface: Darker and more green than, but closest to 146B; flushed and striated with 187A, striations most prominent towards the base. Venation, upper and lower surfaces: Same as lamina.

Inflorescence description:

*Inflorescence form.*—Terminal inflorescences with about nine lateral panicles subtended by showy primary bracts; inflorescences supported on erect and strong scapes.

*Inflorescence longevity.*—Inflorescences of the new Guzmania are very long-lasting; bract coloration is maintained for about two to three months in an interior environment. Inflorescences persistent.

*Natural flowering season and time to flower.*—Plants flower throughout the year and begin to flower about 13 to 16 weeks after floral induction.

*Flowers.*—Arrangement: Single flowers at the terminal of the inflorescence and in lateral panicles. Quantity per flower spike: About 150 flowers and flower buds. Corolla: Arrangement: Three petals, gameopetalous. Length: About 3.4 cm. Width: About 5 mm. Color (both surfaces): 4D. Calyx: Arrangement: Three petals, gameosepalous. Length: About 2.4 cm. Width: About 7 mm. Color (both surfaces): 155B flushed with 67A to 67B. Reproductive organs: Stamens: Quantity per flower: Six. Filament length: About 2.6 cm. Anther length: About 5 mm. Anther color: Brown black. Pistils: Style length: About 3.4 cm. Style color: 145D. Ovary: Superior with three locules. Length: About 7 mm. Color: 145D.

*Bracts.*—Arrangement: Terminal bracts at the terminal; primary bracts subtend and cover the lateral panicles; and scape bracts spirally clasp the scape. Quantity per flower spike, terminal bracts: About 20. Quantity per flower spike, primary bracts: About 13. Quantity per flowr spike, scape bracts: About 13. Shape, terminal and primary bracts: Ovate with cuspidate apices; margin, entire. Shape, scape bracts: Lanceolate with acute apices; margins, entire. Length, terminal bracts: About 3.2 cm. Length, primary bracts: About 3.5 to 4 cm. Length, scape bracts: About 7 to 17 cm. Width, terminal bracts: About 1.3 cm. Width, primary bracts: About 2.6 to 3.3 cm. Width, scape bracts: About 1 to 2.8 cm. Texture, all bracts, upper and lower surfaces: Leathery; smooth. Color: Terminal bracts, upper and lower surfaces: 64B to 67A; towards the base, streaked with white, close to 155D. Primary bracts, upper and lower surfaces: 64D to 67A. Scape bracts, upper and lower surfaces: 64B; lower scape bracts, 137A.

*Scape.*—Strength: Strong. Aspect: Typically erect. Length: About 43 cm. Diameter: About 1.2 cm. Texture: Smooth. Color: Portions exposed to light, 67B; portions not exposed to light, 150D.

*Seed/fruit.*—Seed and fruit production has not been observed.

Temperature tolerance: Plants of the new Guzmania have been observed to tolerate temperatures from about 50 to 100° F.

Disease/pest resistance: Plants of the new Guzmania have not been observed to resistant to pathogens and pests common to Guzmania.

It is claimed:

1. A new and distinct cultivar of Guzmania plant named 'Viola', as illustrated and described.

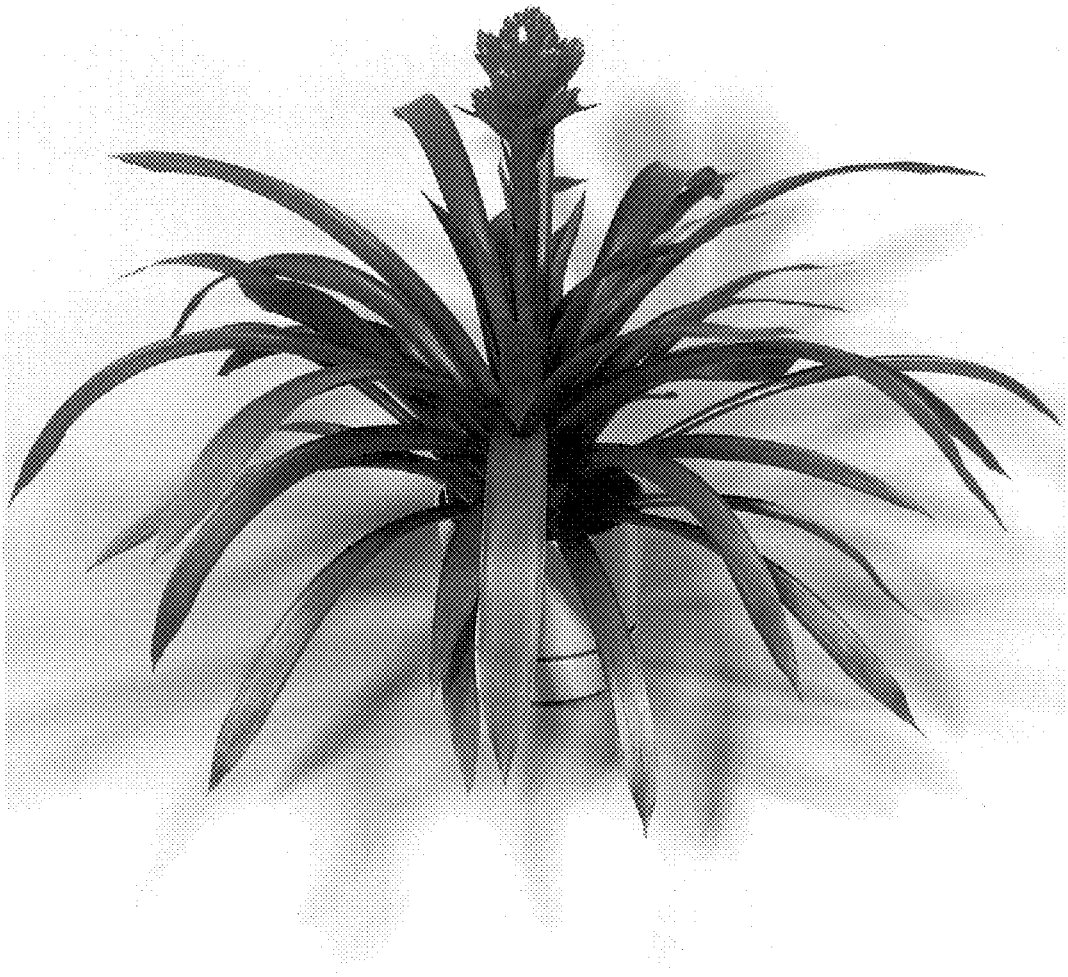

* * * * *